United States Patent
Arakawa (10) Patent No.: US 10,418,732 B2
(45) Date of Patent: Sep. 17, 2019

(54) BOARD ATTACHING STRUCTURE

(71) Applicant: OLYMPUS CORPORATION, Hachioji-shi, Tokyo (JP)

(72) Inventor: Naoki Arakawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/119,658

(22) Filed: Aug. 31, 2018

(65) Prior Publication Data

US 2018/0375236 A1 Dec. 27, 2018

Related U.S. Application Data

(63) Continuation of application No. PCT/JP2017/033698, filed on Sep. 19, 2017.

(30) Foreign Application Priority Data

Dec. 20, 2016 (JP) .................................. 2016-246487

(51) Int. Cl.
| | |
|---|---|
| *H01R 12/71* | (2011.01) |
| *A61B 1/00* | (2006.01) |
| *G02B 23/24* | (2006.01) |
| *H01R 12/73* | (2011.01) |
| *H01R 12/52* | (2011.01) |

(52) U.S. Cl.
CPC ....... *H01R 12/716* (2013.01); *A61B 1/00121* (2013.01); *A61B 1/00124* (2013.01); *G02B 23/2476* (2013.01); *H01R 12/732* (2013.01); *H01R 12/52* (2013.01)

(58) Field of Classification Search
None
See application file for complete search history.

(56) References Cited

U.S. PATENT DOCUMENTS

| | | | |
|---|---|---|---|
| 7,798,839 B2 * | 9/2010 | Kitahara ............ | H01R 13/6315 361/735 |
| 2006/0009048 A1 * | 1/2006 | Hsieh ..................... | H05K 1/147 439/65 |

(Continued)

FOREIGN PATENT DOCUMENTS

| | | |
|---|---|---|
| JP | 2005-129866 A | 5/2005 |
| WO | 2011/052408 A1 | 5/2011 |

OTHER PUBLICATIONS

Dec. 12, 2017 Search Report issued in International Patent Application No. PCT/JP2017/033698.

*Primary Examiner* — Tho D Ta
(74) *Attorney, Agent, or Firm* — Oliff PLC (57) ABSTRACT

A board attaching structure includes a first board on which a first connector provided, a second board on which a second connector provided, a plate-like member extending parallel to the first board and covering at least part of an surface of the first board, a posture restricting portion formed by bending part of the plate-like member toward the first board and configured to restrict a posture of the second board with respect to the first board when the second connector is mounted on the first connector, and a position restricting portion formed by bending part of the plate-like member and configured to restrict a position at which the second board is arranged on the first board while the second connector is mounted on the first connector.

15 Claims, 10 Drawing Sheets

(56) References Cited

U.S. PATENT DOCUMENTS

2012/0202385 A1 8/2012 Miyagi et al.
2014/0094067 A1 4/2014 Kubo
2014/0187060 A1 7/2014 Kubo

* cited by examiner

BOARD ATTACHING STRUCTURE

CROSS-REFERENCE TO RELATED APPLICATIONS

This is a Continuation Application of PCT Application No. PCT/JP2017/033698, filed Sep. 19, 2017, and based upon and claiming the benefit of priority from prior Japanese Patent Application No. 2016-246487, filed Dec. 20, 2016, the entire contents of which are incorporated herein by reference.

BACKGROUND OF THE INVENTION

1. Field of the Invention

The present invention relates to a board attaching structure.

2. Description of the Related Art

For example, US 2014/0187060 A1 discloses an endoscope including a board connection structure (attaching structure) inside a control section. The control section incorporates a first board arranged inside a housing case (plate-like member) and a second board detachably attached to the first board. The first board and the second board each are provided with an electrical circuit and a connector. These connectors are coupled to each other to electrically connect the first board to the second board.

BRIEF SUMMARY OF THE INVENTION

According to one aspect of the invention, a board attaching structure including a first board formed in a plate shape, a first connector provided on an surface of the first board, a second board formed in a plate shape, a second connector provided on the second board and connected to the first connector to mount the second board on the first board, a plate-like member extending parallel to the first board and covering at least part of the surface of the first board, a posture restricting portion formed by bending part of the plate-like member toward the first board and configured to restrict a posture of the second board with respect to the first board when the second connector is mounted on the first connector, and a position restricting portion formed by bending part of the plate-like member and configured to restrict a position at which the second board is arranged on the first board while the second connector is mounted on the first connector.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
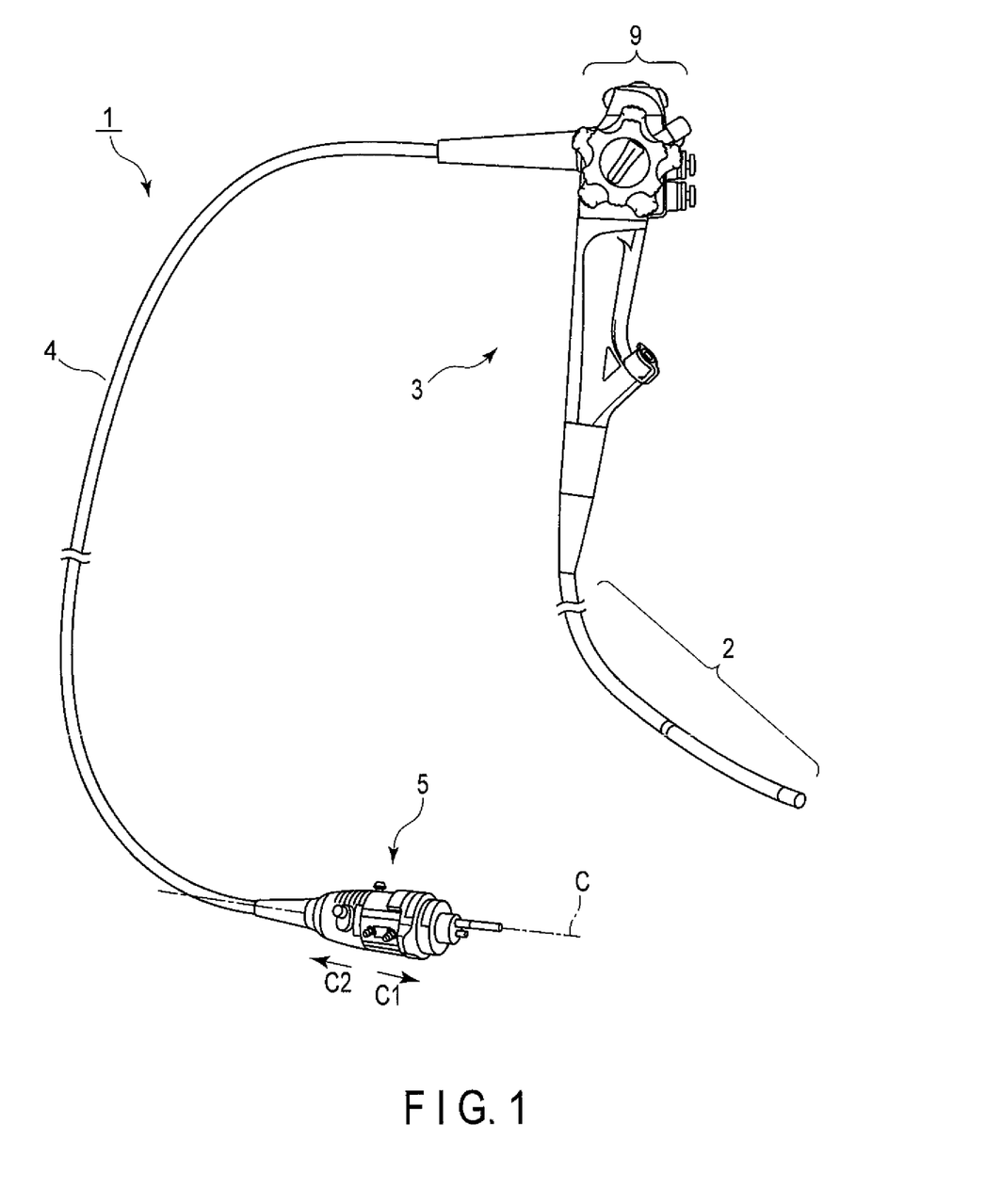
FIG. 1 is a schematic view showing an endoscope according to an embodiment.

An embodiment of the present invention will be described with reference to FIGS. 1 to 11. FIG. 1 shows an endoscope 1 as an insertion device. As shown in FIG. 1, the endoscope 1 includes an insertion portion 2 to be inserted into an observation target region such as a lumen. A control section 3 is connected to the proximal end of the insertion portion 2. A universal cable 4 extends from a side surface of the control section 3. An end portion of the universal cable 4 is provided with an endoscope connector 5. The control section 3 and the endoscope connector 5 are electrically connected to each other via the universal cable 4. The endoscope connector 5, the universal cable 4, the control section 3, and the insertion portion 2 incorporate a plurality of tubes for suction, insufflation, water delivery, and the like in addition to an illumination optical system and an observation optical system. A board attaching structure 6 (to be described later) is arranged in the endoscope connector 5.

The endoscope connector 5 can be detachably connected to an external device (not shown) including a light source device and a processor. This electrically connects the endoscope 1 to the external device via the endoscope connector 5. Power is then supplied from the external device to the endoscope 1 and/or electrical signals and light are transmitted from an external device and the endoscope 1.

Note that the control section 3 has various types of switches 9 for properly operating the observation optical system. Electrically connecting the endoscope 1 to an external device can properly control the observation optical system by operating one of the switches 9. In addition, the endoscope 1 may also be optically connected to an external device via the endoscope connector 5.

The endoscope connector 5 has a longitudinal axis C. In this case, a direction along the longitudinal axis C and a direction almost parallel to the longitudinal axis C are defined as longitudinal directions. Assume that one side in the longitudinal axis is defined as a distal end side (the arrow C1 side in FIG. 1), and a side opposite to the distal end side is defined as a proximal end side (the arrow C2 side in FIG. 1).

Figure 2:
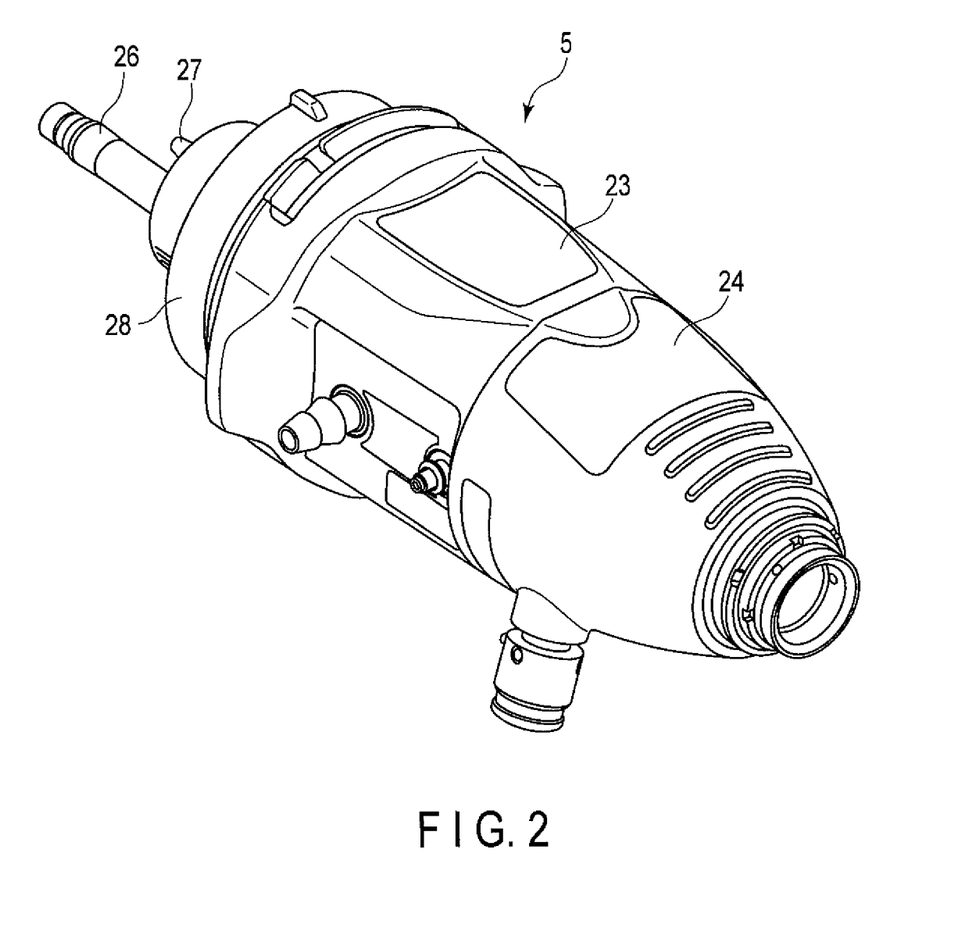
FIG. 2 is a perspective view showing an endoscope connector according to the embodiment.

FIG. 2 shows the arrangement of the endoscope connector 5. As shown in FIG. 2, the distal end portion of the endoscope connector 5 is provided with a connection member 28 connected to an external device. The proximal end side of the connection member 28 is provided with a connector case 23 having an almost cylindrical shape extending along the longitudinal axis. A tubular connector cover 24 is fixed to the proximal end side of the connector case 23 along the longitudinal axis. One end (a distal tip relative to the control section 3) of the universal cable 4 is connected to the proximal end portion of the connector cover 24.

The distal end face of the connection member 28 is provided with a light guide mouth ring 26 and an insufflation mouth ring 27. Light with which an observation target is irradiated at the distal end portion of the insertion portion 2 is supplied from an external device (light source) to the light guide mouth ring 26. A gas to be insufflated at the distal end portion of the insertion portion 2 is supplied from an external device to the insufflation mouth ring 27. Although an example of providing the light guide mouth ring 26 to the distal end face of the connection member 28 will be described below, the light guide mouth ring 26 is not necessary when the illumination optical system includes a light-emitting element such as an LED in the endoscope 1.

Figure 3:
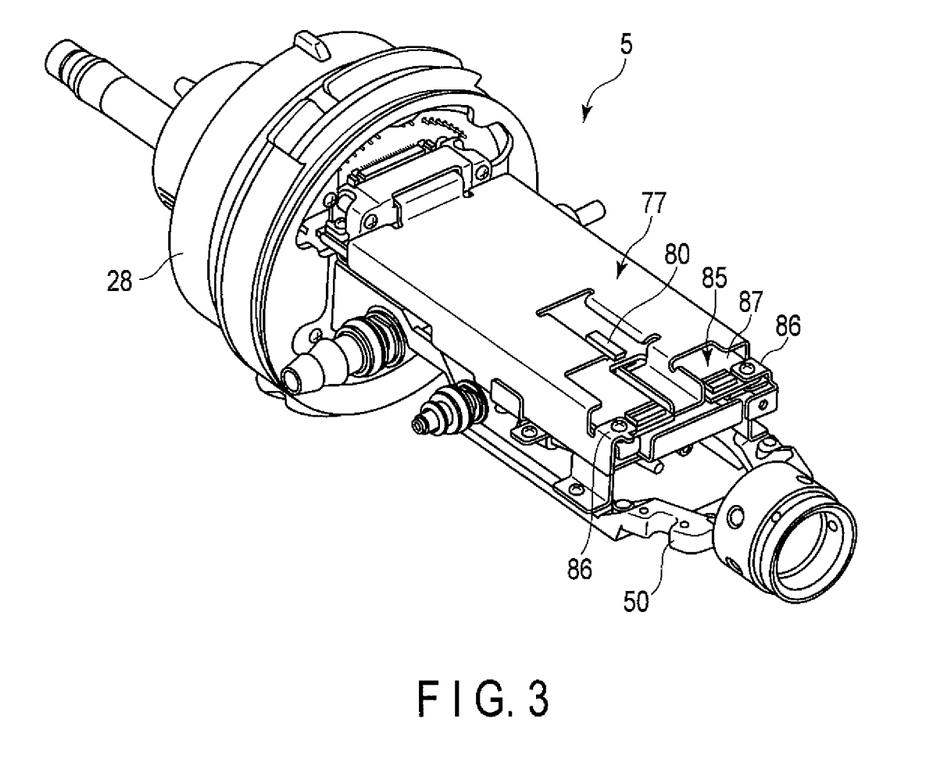
FIG. 3 is a perspective view showing the internal arrangement of the endoscope connector according to the embodiment.

FIG. 3 shows a state in which the connector case 23 and the connector cover 24 are detached from the endoscope connector 5 shown in FIG. 2. As shown in FIG. 3, a main frame 50 is fixed to the connection member 28 with screws or the like (not shown). The main frame 50 is attached to the proximal end side of the connection member 28. The main frame 50 extends along the longitudinal direction and is formed from a metal material such as stainless steel.

A first board 85 is fixed to the connection member 28. The first board 85 is attached to the proximal end side of the connection member 28. The first board 85 is a plate-like (flat plate shape) member extending along the longitudinal direction. The first board 85 and the main frame 50 are arranged to be almost parallel to each other. An electrical circuit is formed on the surface of the first board 85. The first board 85 is coupled to the connection member 28. At this time, a connector 89 (see FIGS. 6 and 8) of the first board 85 is electrically connected to a connector (not shown) of the connection member 28.

Figure 4:
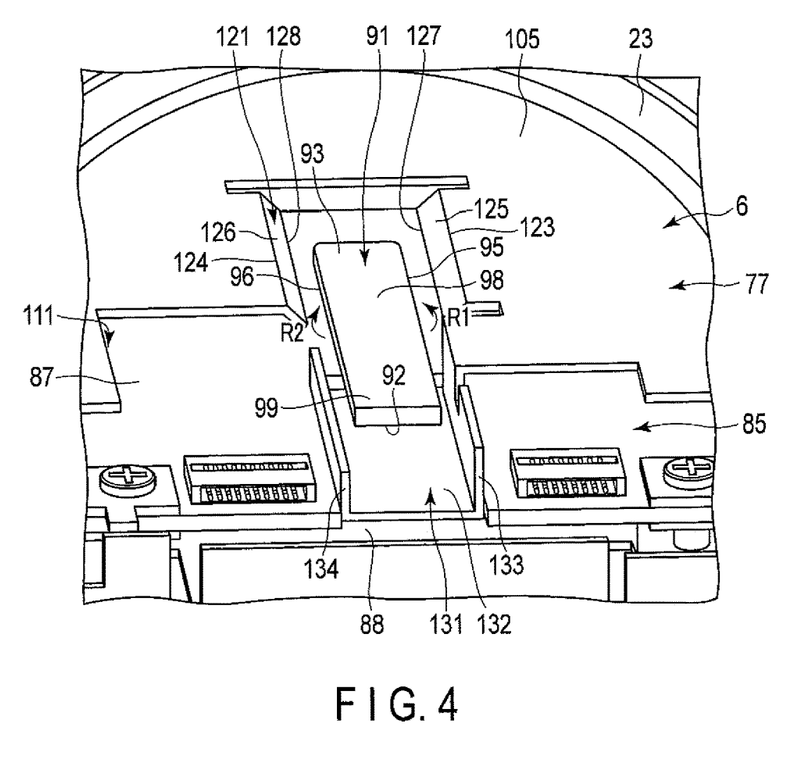
FIG. 4 is a perspective view schematically showing a state in which a second board is mounted on a first board according to the embodiment.
Figure 5:
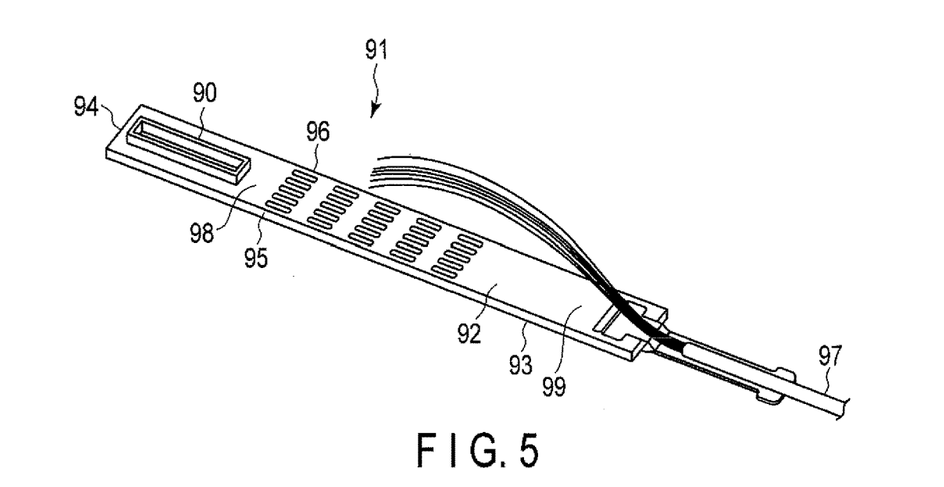
FIG. 5 is a perspective view showing the second board according to the embodiment.

The first board 85 has a principal surface (upper surface) 87. The principal surface 87 is a surface that extends along the longitudinal direction and faces the opposite side to the side where the main frame 50 is arranged. The principal surface 87 is provided with a first connector 80. The first connector 80 is formed into an elongated shape whose size in the widthwise direction is smaller than the size in the longitudinal direction. The first connector 80 is electrically connected to an electrical circuit on the first board 85. As shown in FIGS. 4 and 5, a second connector 90 provided on a second board (mount connector board) 91 is detachably attached to the first connector 80. The second board 91 and the second connector 90 will be described later.

A shield case 77 is attached to the connection member 28. The shield case 77 is fixed to the first board 85 and is used as an electromagnetic shield for the first board 85. The shield case 77 is formed to be almost parallel to the first board 85. The shield case 77 is formed by processing a flat plate (plate-like member) formed from a material having conductivity such as a metal. The shield case 77 is fixed to the first board 85 with a plurality of fixing portions 86. The shield case 77 covers part of the first board 85.

Figure 6:
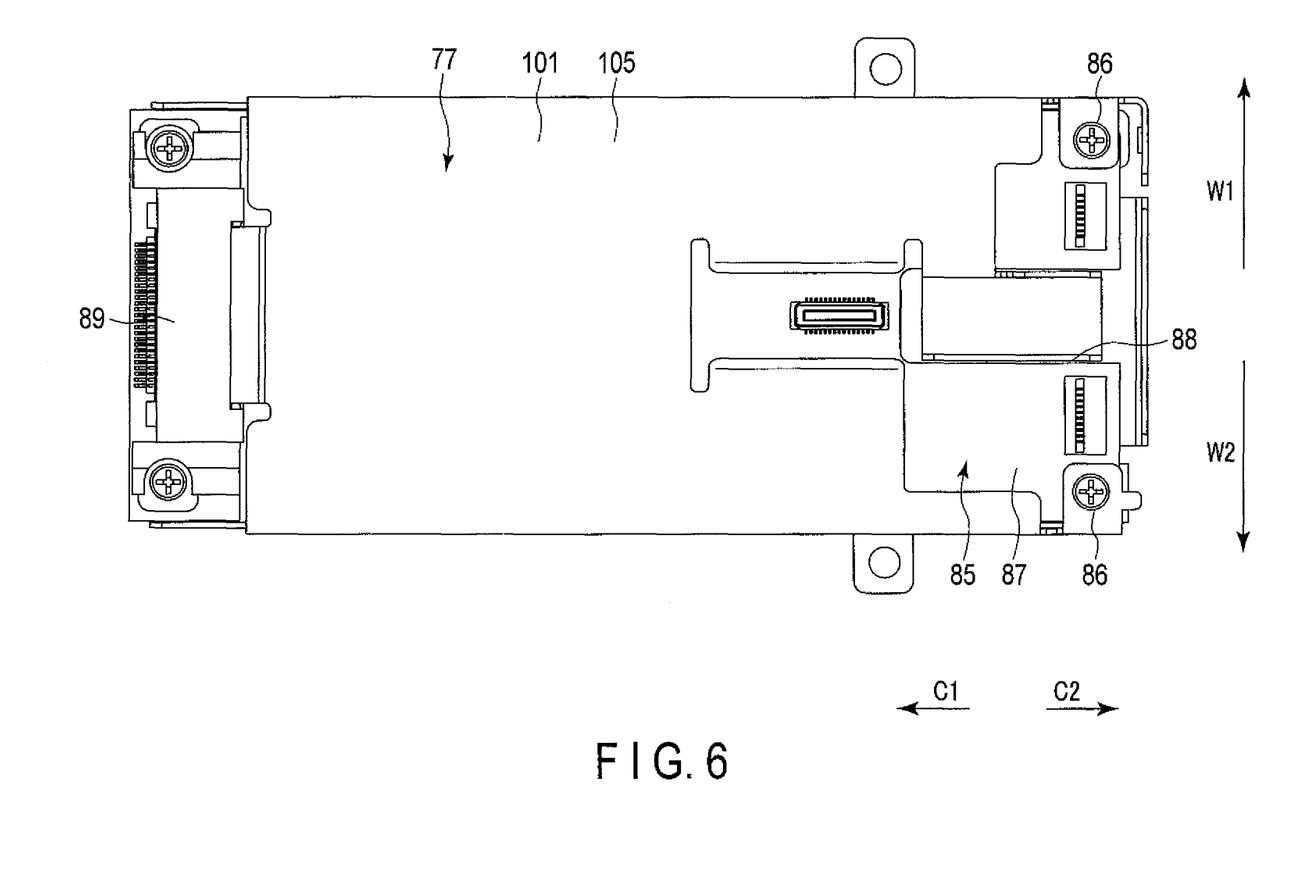
FIG. 6 is a top view showing the first board and a shield case according to the embodiment.
Figure 7:
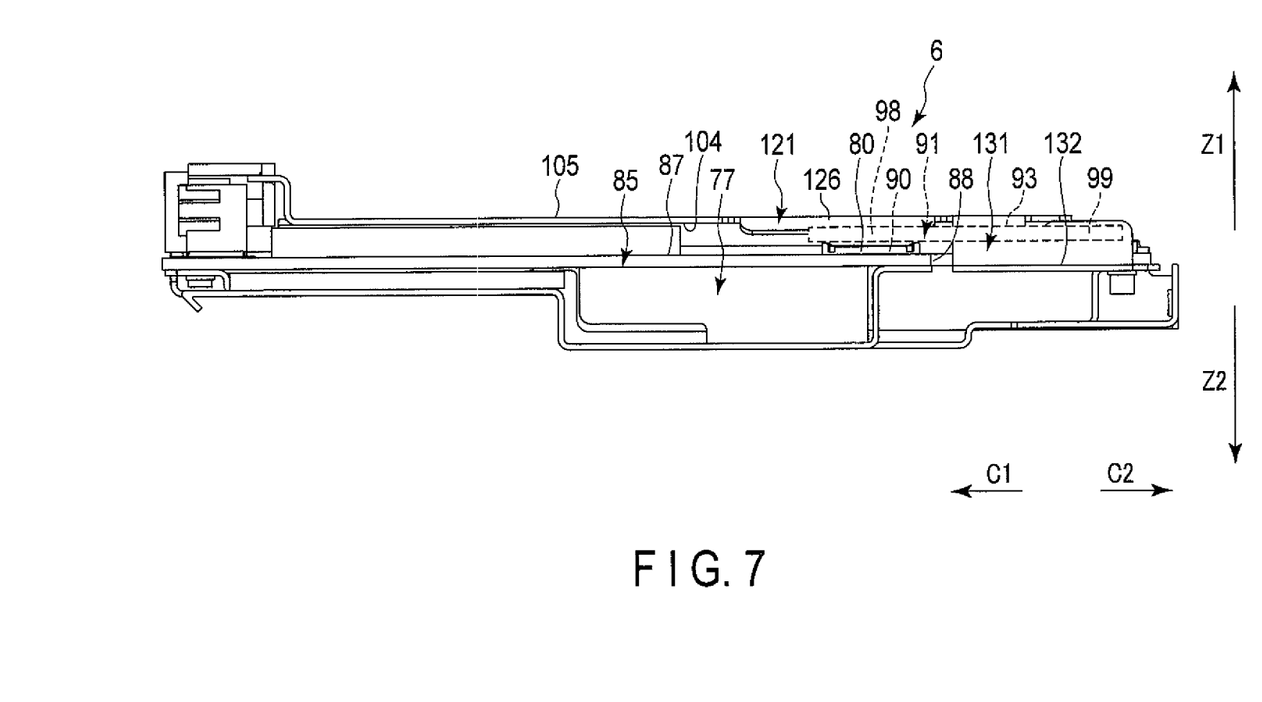
FIG. 7 is a side view showing the first board and the shield case according to the embodiment.

FIGS. 6 and 7 show the first board 85 and the shield case 77. In this case, a direction almost perpendicular to the longitudinal direction and almost perpendicular to the first board 85 is defined as an up-down direction. Of two sides in the up-down direction, the side facing the principal surface 87 is defined as the upper side (the arrow Z1 side in FIG. 7), and the lower side on the opposite side to the up direction is defined as the lower side (the arrow Z2 side in FIG. 7). In addition, a direction almost perpendicular to the longitudinal direction and almost perpendicular to the up-down direction is defined as the widthwise direction. Of two sides in the widthwise direction, one side is defined as the right side (the arrow W1 side in FIG. 6), and the side opposite to the right side is defined as the left side (the arrow W2 side in FIG. 6).

FIG. 4 shows a state in which the second board 91 is mounted on the first board 85. FIG. 5 shows the second board 91. As shown in FIGS. 4 and 5, the second board 91 is a plate (flat plate) having an almost rectangular shape with an elongated surface. The second board 91 is detachably mounted on the first board 85 through the first connector 80 and the second connector 90. An electrical circuit is formed on the second board 91. The second board 91 includes an opposed surface 92 that faces the principal surface 87 of the first board 85 when the second board 91 is mounted on the first board 85 through the first connector 80 and the second connector 90 and an outer surface 93 facing the opposite side to the opposed surface 92. The surface area of the opposed surface 92 is smaller than that of the principal surface 87 of the first board 85. In addition, the second board 91 includes a distal end face 94 facing the distal end side when the second board 91 is mounted on the first board 85, a side surface 95 facing the right side, and a side surface 96 facing the left side.

As shown in FIG. 5, the second board 91 includes a connector arrangement portion 98 and a holding portion 99. The connector arrangement portion 98 and the holding portion 99 are arranged side by side along the longitudinal direction of the second board 91. The opposed surface 92 of the connector arrangement portion 98 is provided with the second connector 90. The second connector 90 is formed into an elongated shape whose size in a direction (the widthwise direction of the second board 91) almost perpendicular to the longitudinal direction of the second board 91 is smaller than that in the longitudinal direction. The second connector 90 is preferably provided on a middle portion of the opposed surface 92 in the widthwise direction. The second connector 90 is electrically connected to the electrical circuit on the second board 91. The second connector 90 is detachably coupled to the first connector 80 provided on the principal surface 87 of the first board 85. Coupling the first connector 80 to the second connector 90 will couple the first board 85 to the second board 91 and electrically connect the first board 85 to the second board 91. Note that the male and female parts of the first connector 80 and the second connector 90 are set as appropriate.

One end of an electrical cable (signal cable) 97 is attached to the holding portion 99. One end of the electrical cable (signal cable) 97 is electrically connected to the electrical circuit on the second board 91. The other end of the electrical cable 97 is electrically connected to, for example, the switch 9 of the control section 3 through the universal cable 4. Accordingly, the electrical circuit on the second board 91 is electrically connected to the control section 3.

As described above, the control section 3 is electrically connected to the electrical circuit on the second board 91, and the electrical circuit on the second board 91 is electrically connected to the electrical circuit on the first board 85. The electrical circuit on the first board 85 is electrically connected to the connection member 28. Accordingly, the control section 3 is electrically connected to the connection member 28 of the endoscope connector 5. This makes it possible to electrically connect an external device connected to the endoscope connector 5 to the control section 3.

Accordingly, the external device is properly controlled in accordance with the operation of the switch 9 of the control section 3.

Figure 8:
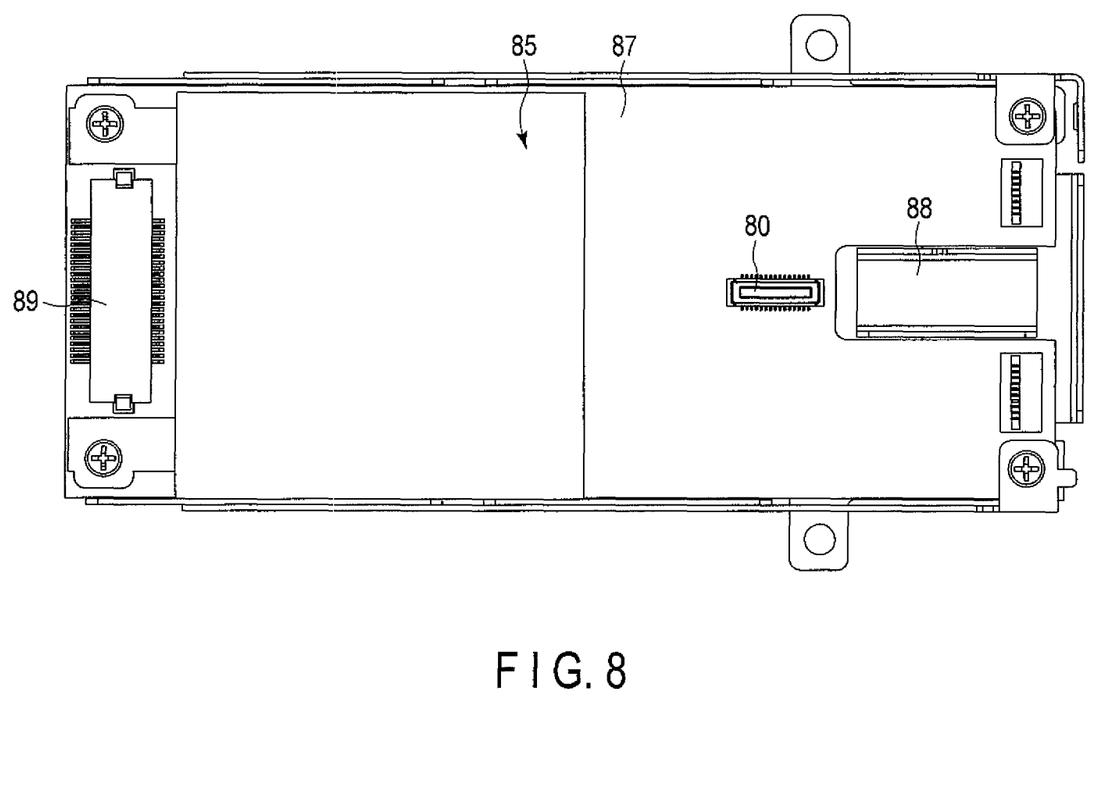
FIG. 8 is a top view showing the first board according to the embodiment.

FIG. 8 shows the first board 85. FIG. 8 shows a state in which the shield case 77 in the state shown in FIG. 6 is detached. As shown in FIG. 8, the first connector 80 is provided on a middle portion in the widthwise direction. A notched portion 88 is formed in the proximal end portion of the first board 85. The notched portion 88 is concaved from the proximal end to the distal end side of the first board 85 along the longitudinal direction. The notched portion 88 is provided in a middle portion in the widthwise direction. The notched portion 88 is located closer to the proximal end side than the first connector 80 along the longitudinal direction.

In this case, the first connector 80 and the notched portion 88 are provided on a middle portion of the first board 85 in the widthwise direction. However, this is not exhaustive. For example, the first connector 80 and the notched portion 88 may be provided at a position slightly shifted to the right side from the middle portion or at a position slightly shifted to the left side from the middle portion.

Figure 9:
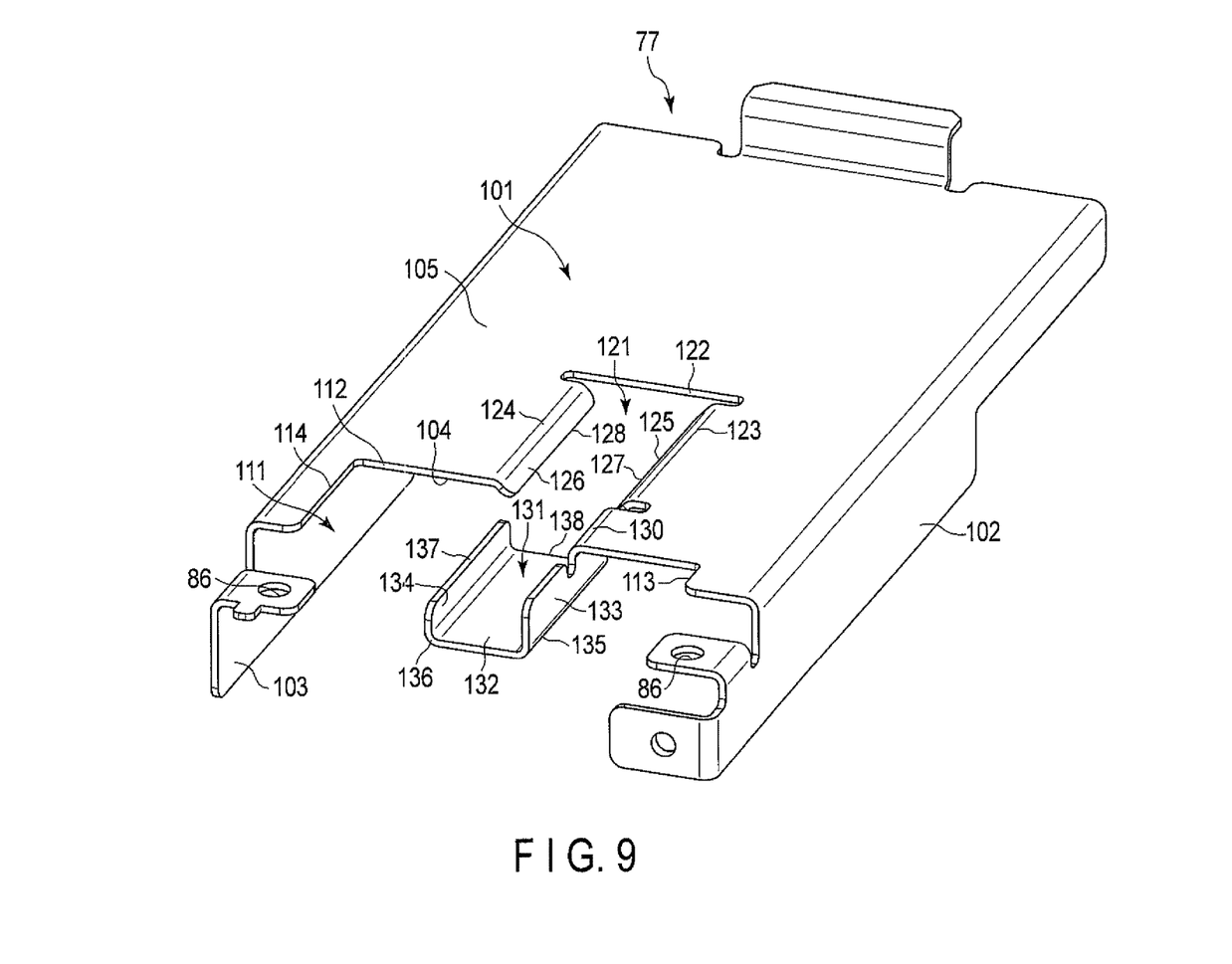
FIG. 9 is a perspective view showing the shield case according to the embodiment.

FIG. 9 shows the shield case 77. As shown in FIG. 9, the shield case 77 includes a main body portion 101 extending almost parallel to the first board 85. On the right side of the main body portion 101, a side surface portion 102 is formed by bending the shield case 77 to the first board 85 side (lower side) along the longitudinal direction. On the left side of the main body portion 101, a side surface portion 103 is formed by bending the shield case 77 to the first board 85 side (lower side) along the longitudinal direction. The side surface portions 102 and 103 extend along the longitudinal direction and are formed to be almost perpendicular to the main body portion 101. The main body portion 101 and the side surface portions 102 and 103 are integrally formed. The first board 85 is arranged between the side surface portions 102 and 103 and fixed to the shield case 77 at fixing portions 86.

The main body portion 101 includes an opposed surface 104 facing the principal surface 87 of the first board 85 and an outer surface 105 facing the opposite side to the opposed surface 104. The opposed surface 104 is a flat surface facing downward. The outer surface 105 is a flat surface facing upward, and forms part of the outer surface of the shield case 77.

Various elements are arranged between the shield case 77 and the first board 85. Accordingly, as shown in FIG. 7, an appropriate gap is formed between the opposed surface 104 of the shield case 77 and the principal surface 87 of the first board 85. Accordingly, the opposed surface 104 of the shield case 77 is spaced apart from the principal surface 87 of the first board 85. While the second board 91 indicated by the broken line in FIG. 7 is mounted on the first board 85, the outer surface 105 of the main body portion 101 of the shield case 77 is located above the outer surface 93 of the second board 91. That is, while the second connector 90 is mounted on the first connector 80, the outer surface 93 of the second board 91 which faces the opposite side to the opposed surface 92 facing the first board 85 is closer to the first board 85 than the outer surface 105 of the shield case 77 which faces the opposite side to the opposed surface 104 facing the first board 85.

The main body portion 101 includes a notched portion 111 that is concaved from the proximal end of the main body portion 101 toward the distal end side. The notched portion 111 includes a distal end side edge portion 112 extending along the widthwise direction, and a right side edge portion 113 and a left side edge portion 114 that extend from the proximal end of the main body portion 101 toward the distal end side along the longitudinal direction. The distal end of the left side edge portion 114 is continuous with the left end of the distal end side edge portion 112. As shown in FIG. 6, part of the principal surface 87 of the first board 85 is exposed outward from the notched portion 111.

The main body portion 101 includes a guiding portion 121. The guiding portion 121 is provided on the proximal end side of the notched portion 111. The distal end side edge portion 112 of the notched portion 111 is partially concaved toward the distal end side in the guiding portion 121. The guiding portion 121 is an almost U-shaped groove that opens toward the proximal end side. The notched portion 111 and the guiding portion 121 are continuous along the longitudinal direction. The distal end side edge portion 112 of the notched portion 111 partially opens toward the proximal end side.

The main body portion 101 includes a restricting portion 131. The restricting portion 131 is integrally formed with the main body portion 101 of the shield case 77. The restricting portion 131 is arranged in the notched portion 111. The restricting portion 131 is formed by bending part of the plate-like member forming the shield case 77 upon cutting or forming slits. The restricting portion 131 is formed by bending, at a bent portion 130, a portion extending from part of the right side edge portion 113 of the notched portion 111 to the left side. The restricting portion 131 extends along the longitudinal direction and is formed into an almost U shape that opens toward the upper side. In addition, the restricting portion 131 is arranged on the proximal end side of the guiding portion 121.

The restricting portion 131 includes a bottom portion 132, a first side wall 133, and a second side wall 134. The first side wall 133 extends from the bent portion 130 of the notched portion 111 to the lower side so as to be almost perpendicular (orthogonal) to the main body portion 101. The bottom portion 132 is a flat surface formed parallel or almost parallel to the opposed surface 104 and the outer surface 105 of the main body portion 101. The bottom portion 132 is almost perpendicular to the first side wall 133 and extends from the lower end of the first side wall 133 toward the left side. The second side wall 134 extends from the left end of the bottom portion 132 toward the upper side so as to be almost perpendicular (orthogonal) to the bottom portion 132 and the main body portion 101. Accordingly, the bottom portion 132 is located between the first side wall 133 and the second side wall 134 in the widthwise direction. A corner portion 135 is formed at a continuous portion between the first side wall 133 and the bottom portion 132. In addition, a corner portion 136 is formed at the continuous portion between the second side wall 134 and the bottom portion 132. A distal end 138 of the restricting portion 131 is located on the proximal end side than the distal end side edge portion 112 of the notched portion 111.

The first side wall 133 is formed by bending an extended portion from the right side edge portion 113 of the notched portion 111. Accordingly, at the position where the restricting portion 131 is provided in the longitudinal direction, the main body portion 101, the right side edge portion 113, the bent portion 130, the first side wall 133, the bottom portion 132, and the second side wall 134 are continuously formed in the order named from the right side to the left side in the widthwise direction. They are integrally formed by bending continuous portions between the respective components such that one portion of each component is almost perpendicular to the other portion.

The sum of the length of the first side wall 133 in the up-down direction (the length from the bent portion 130 to the corner portion 135), the length of the bottom portion 132 in the widthwise direction (the length between the corner portions 135 and 136), and the length of the second side wall 134 in the up-down direction (the length from the corner portion 136 to an upper end 137 of the second side wall 134) is smaller than the length between the bent portion 130 of the notched portion 111 and the left side edge portion 114 in the widthwise direction. If the bents between the portions at the bent portion 130 and the corner portions 135 and 136 are stretched so as to form a main body portion 101, the side walls 133 and 134, and the bottom portion 132 into one flat plate, the upper end 137 forming the left end of the restricting portion 131 is located on the right side of the left side edge portion 114. For this reason, the restricting portion 131 does not come into contact with the left side edge portion 114. In addition, as described above, the restricting portion 131 does not come into contact with the distal end side edge portion 112 because the distal end 138 of the restricting portion 131 is located on the proximal end side than the distal end side edge portion 112 of the notched portion ill. Accordingly, the restricting portion 131 can be formed integrally with the main body portion 101 by processing one plate-like member (flat plate).

As shown in FIG. 7, while the shield case 77 is attached to the first board 85, the restricting portion 131 is arranged in the notched portion 88 of the first board 85. In this case, the bottom portion 132 of the restricting portion 131 is located below the principal surface 87 of the first board 85.

As shown in FIGS. 4 and 7, while the second board 91 is mounted on the first board 85, the holding portion 99 of the second board 91 is arranged between the side walls 133 and 134 of the restricting portion 131. In this case, the opposed surface 92 of the holding portion 99 faces the bottom portion 132 of the restricting portion 131. The side surface 95 of the holding portion 99 faces the first side wall 133 of the restricting portion 131. In addition, the side surface 96 of the holding portion 99 faces the second side wall 134 of the restricting portion 131. That is, the side walls 133 and 134 have a pair of wall surfaces facing the side surfaces 95 and 96 of the second board 91 while the second connector 90 is mounted on the first connector 80. In addition, the distance between the side walls 133 and 134 in the widthwise direction is slightly larger than the width of the holding portion 99 of the second board 91.

The opposed surface 92 of the holding portion 99 of the second board 91 is spaced apart from the bottom portion 132 of the restricting portion 131. This forms a gap between the opposed surface 92 of the second board 91 and the bottom portion 132 of the restricting portion 131. The electrical cable 97 and the like to be provided on the opposed surface 92 of the second board 91 are arranged in this gap.

The guiding portion 121 includes a distal end side edge portion 122 extending at the distal end of the guiding portion 121 along the widthwise direction, and a bent portion 123 and a bent portion 124 extending from the distal end side edge portion 122 toward the distal end side along the longitudinal direction.

The guiding portion 121 includes an inclined portion 125 extending from the bent portion 123 to the left side and an inclined portion 126 extending from the bent portion 124 to the right side. The inclined portions 125 and 126 are inclined with respect to the outer surface 105 of the main body portion 101. The inclined portions 125 and 126 are smoothly inclined downward from the bent portions 123 and 124 to the center in the widthwise direction. The inclined portions 125 and 126 are formed by bending part of the main body portion 101 of the shield case 77 downward at the bent portions 123 and 124.

Note that the distal end of the bent portion 123 is spaced apart from the right side end portion of the distal end side edge portion 122, and the distal end of the bent portion 124 is spaced apart from the left side end portion of the distal end side edge portion 122. This prevents deformation near the right side end portion and the left side end portion of the distal end side edge portion 122 when the bent portions 123 and 124 are formed by processing part of the main body portion 101.

As shown in FIGS. 4 and 7, while the shield case 77 is attached to the first board 85, the inclined portions 125 and 126 are inclined from the main body portion 101 toward the principal surface 87 of the first board 85. In addition, lower ends 127 and 128 of the inclined portions 125 and 126 are formed to be located above the principal surface 87 of the first board 85.

The shield case 77 opens toward the upper side and the proximal end side at the guiding portion 121. Part of the principal surface 87 of the first board 85 is exposed outward from the guiding portion 121 toward the upper side and the proximal end side. In addition, the first connector 80 provided on the principal surface 87 of the first board 85 is exposed outward from between the inclined portions 125 and 126 toward the upper side and the proximal end side. That is, the first connector 80 is exposed outward through the guiding portion 121. The first connector 80 is preferably provided on a middle portion between the lower ends 127 and 128 of the inclined portions 125 and 126 shown in FIG. 4.

While the second board 91 is mounted on the first board 85, the connector arrangement portion 98 of the second board 91 is arranged between the inclined portions 125 and 126 at the guiding portion 121. In this case, the side surface 95 of the connector arrangement portion 98 faces the inclined portion 125 of the guiding portion 121. In addition, the side surface 96 of the connector arrangement portion 98 faces the inclined portion 126 of the guiding portion 121. That is, while the second connector 90 is mounted on the first connector 80, the inclined portions 125 and 126 have a pair of wall surfaces facing the side surfaces 95 and 96 of the second board 91. In addition, the distance between the lower end 127 of the inclined portion 125 and the lower end 128 of the inclined portion 126 in the widthwise direction is slightly larger than the width of the connector arrangement portion 98 of the second board 91. Note that the distance between the lower end 127 of the inclined portion 125 and the lower end 128 of the inclined portion 126 in the widthwise direction is smaller than, for example, the pulp of a finger (for example, a normal size forefinger of an adult male). In addition, the distance between the bent portion 123 and the bent portion 124 in the widthwise direction is larger than the width of the pulp of a finger (for example, a forefinger).

At the guiding portion 121, the sum of the length of the inclined portion 125, the length from the bent portion 123 to the lower end 127, the length of the inclined portion 126, and the length from the bent portion 124 to the lower end 128 is smaller than the distance between the bent portion 123 and the bent portion 124. That is, the sum of the lengths of the extensions of the inclined portions 125 and 126 is smaller than the distance between the bent portion 123 and the bent portion 124. Accordingly, if the bents between the portions at the bent portion 123 and the bent portion 124 are stretched so as to form the main body portion 101 and inclined portions 125 and 126 into one flat plate, the lower end 127 of the inclined portion 125 and the lower end 128 of the inclined portion 126 face each other but do not come into contact with each other. For this reason, the guiding portion 121 can be formed integrally with the main body portion 101 by processing one flat plate.

As described above, while the second board 91 is mounted on the first board 85, the holding portion 99 of the second board 91 is arranged at the restricting portion 131 of the shield case 77, and the connector arrangement portion 98 of the second board 91 is arranged at the guiding portion 121 provided on the distal end side of the restricting portion 131. Accordingly, while the second board 91 is mounted on the first board 85, the holding portion 99 is located at the proximal end portion of the second board 91, and the connector arrangement portion 98 is located at the distal end portion of the second board 91.

The functions and effects of this embodiment will be described next. When the endoscope connector 5 is manufacture, the connector case 23 is attached to the connection member 28, and the exterior of the endoscope connector 5 is formed by the connection member 28 and the connector case 23. The first board 85 to which the main frame 50 and the shield case 77 are attached is fixed to the connection member 28. The second board 91 is then mounted on the first board 85.

Figure 10:
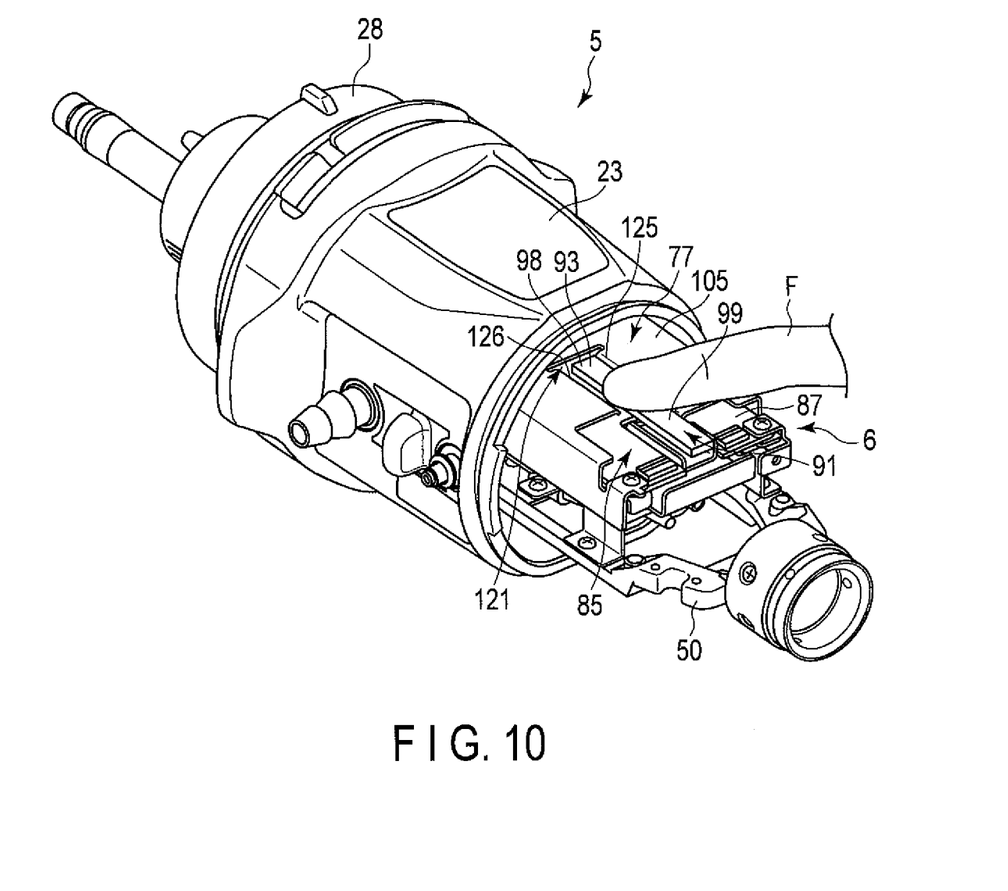
FIG. 10 is a schematic view showing how the second board is mounted on the first board by being pushed with a finger according to the embodiment.

FIG. 10 shows how the second board 91 is attached to the first board 85. When mounting the second board 91 on the first board 85, the operator holds the holding portion 99 of the second board 91 and inserts the connector arrangement portion 98 of the second board 91 from the proximal end side to the distal end side of the endoscope connector 5 along the outer surface 105 of the shield case 77. The operator then arranges the connector arrangement portion 98 and second connector 90 of the second board 91 on the first connector 80 of the first board 85, and presses the outer surface 93 of the connector arrangement portion 98 downward toward the first board 85 with the pulp of his/her finger (for example, a forefinger) F. This couples the first connector 80 to the second connector 90. In this case, the second board 91 is a very small component compared with the endoscope connector 5 and the first board 85. This makes it difficult to recognize the attaching position of the second board 91 with respect to the first board 85 and to arrange the second board 91 at an appropriate position with respect to the first board 85.

In this embodiment, the shield case 77 is provided with the guiding portion 121. The first connector 80 is exposed from the shield case 77 to the upper side and the distal end side at the guiding portion 121. This allows the operator to visually recognize the position of the first connector 80 with respect to the shield case 77 and the first board 85. That is, making the attaching position of the second board 91 on the outer surface 105 of the shield case 77 open allows the operator to visually recognize the attaching position of the second board 91. This makes it easy to attach the second board 91 to the first board 85.

The gap between the inclined portion 125 and the inclined portion 126 is slightly larger than the width of the connector arrangement portion 98 of the second board 91. This allows the operator to arrange the second connector 90 at an appropriate position with respect to the first connector 80 by arranging the distal end portion of the second board 91 between the inclined portion 125 and the inclined portion 126. This restricts the posture of the second board 91 with respect to the first board 85 and arranges the second board 91 at an appropriate position with respect to the first board 85. In addition, the first connector 80 is spaced apart from the inclined portion 125 and the inclined portion 126 at a middle portion between the inclined portion 125 and the inclined portion 126. The second connector 90 is provided on a middle portion of the connector arrangement portion 98 of the second board 91 in the widthwise direction. Accordingly, arranging the second board 91 on the middle portion between the inclined portion 125 and the inclined portion 126 facilitates connecting the second connector 90 to the first connector 80.

Subsequently, the second connector 90 provided on the second board 91 is electrically connected to the first connector 80 provided on the first board 85, and the second board 91 is appropriately mounted on the first board 85.

The guiding portion 121 is a posture restricting portion that is formed by bending part of the shield case 77 toward the first board 85 side and restricts the posture of the second board 91 with respect to the first board 85 when the second connector 90 is attached to the first connector 80. The guiding portion 121 guides the second board 91 to an appropriate position with respect to the first board 85 when the second connector 90 is mounted on the first connector 80.

In order to accurately arrange the second connector 90 at an attaching position with respect to the first connector 80, the distances between the side surfaces 95 and 96 of the second board 91 and the opening edge portions (lower ends 127 and 128) formed by the guiding portion 121 are preferably reduced. That is, the width between the opening edge portions of the guiding portion 121 is preferably minimized while being larger than the width of the second board 91. However, while the second board 91 is arranged on the first board 85, the operator must push the outer surface 93 of the second board 91 to a lower side of the outer surface 105 of the shield case 77. At this time, if the width between the opening edge portions of the guiding portion 121 is too small, the finger F may come into contact with the outer surface 105 of the shield case 77, resulting in failure to sufficiently push the second board 91 with respect to the first board 85.

In this embodiment, the guiding portion 121 is provided with the inclined portions 125 and 126 extending toward the principal surface 87 of the first board 85. The lower ends 127 and 128 of the inclined portions 125 and 126 are spaced apart from each other in the widthwise direction and also spaced apart above the principal surface 87 of the first board 85, thereby forming the opening edge portions of the guiding portion 121 in the widthwise direction. Accordingly, when the operator pushes the outer surface 93 of the second board 91 toward the first board 85, the finger F comes into contact with the pair of inclined portions 125 and 126. When the inclined portions 125 and 126 are pressed downward with the finger F of the operator, the inclined portions 125 and 126 are elastically deformed and curved downward with respect to the outer surface 105 of the shield case 77 as the finger F and the second board 91 move. The opening edge portions of the guiding portion 121 are provided with the inclined portions 125 and 126 that can be curved toward the first board 85. This arrangement makes it possible to push the second board 91 to an appropriate attaching position with the first board 85 by pressing the inclined portions 125 and 126 with the finger F.

The inclined portions 125 and 126 are smoothly inclined from the main body portion 101 at the bent portions 123 and 124. This prevents the finger F of the operator from being caught by the bent portions 123 and 124 by coming into contact with the bent portions 123 and 124.

Accordingly, providing the guiding portion 121 having the inclined portions 125 and 126 allows the operator to accurately arrange the second board 91 at an attaching position on the first board 85 and push the second board 91 to the first board 85 arranged in the shield case 77.

Note that when the state in which the inclined portions 125 and 126 of the guiding portion 121 are pressed downward with the finger F of the operator is released, the inclined portions 125 and 126 is restored to the initial state by elastic deformation.

Figure 11:
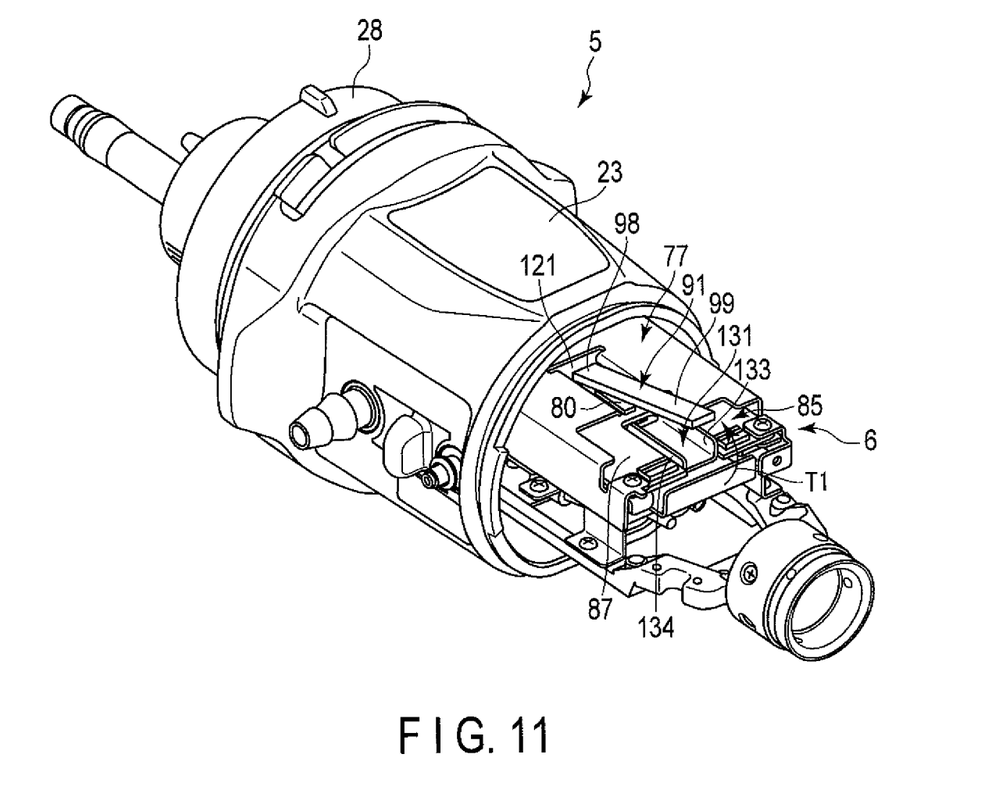
FIG. 11 is a schematic view showing how the second board is detached from the first board according to the embodiment.

At the time of component replacement or repair, the second board 91 is sometimes detached from the first board 85. FIG. 11 shows how the second board 91 is detached from the first board 85. The operator holds the holding portion 99 of the second board 91 by pinching the proximal end of the holding portion 99 of the second board 91 with his/her fingers or a holding tool or the like, and raises the holding portion 99 with respect to the first board 85. The operator then rotates the holding portion 99 about the coupling portion between the connectors 80 and 90 with respect to the first board 85. This releases coupling between the first connector 80 and the second connector 90 and detaches the second board 91 from the first board 85. A regulated detaching direction is set in the coupling structure between the first connector 80 and the second connector 90. The second board 91 is recommended to be detached from the first board 85 by being moved relative to the first board 85 along the regulated detaching direction (the arrow T1 direction in FIG. 11). When the second board 91 is detached from the first board 85 along a direction (for example, the arrow R1 or R2 direction in FIG. 4) other than the regulated detaching direction, unintentional loads can be applied to the connectors 80 and 90.

In this embodiment, the connector arrangement portion 98 of the second board 91 is arranged between the pair of end portions 127 and 128 of the guiding portion 121 of the shield case 77. At this time, the connector arrangement portion 98 of the second board 91 is arranged between the inclined portions 125 and 126. As described above, the end portions 127 and 128 are formed between the inclined portion 125 and the inclined portion 126 in the widthwise direction, and the gap between the end portions 127 and 128 is slightly larger than the width of the connector arrangement portion 98 of the second board 91 and smaller than the width of the pulp of the finger. For this reason, the operator cannot insert his/her finger into the space between the second board 91 and the inclined portion 125 and the space between the second board 91 and the inclined portion 126. Accordingly, the operator cannot detach the second board 91 from the first board 85 by inserting his/her finger into the gap between the guiding portion 121 and the connector arrangement portion 98 of the second board 91.

The holding portion 99 of the second board 91 is arranged between the side walls 133 and 134 of the restricting portion 131 of the shield case 77. For this reason, the side walls 133 and 134 regulate the position of the second board 91 with respect to the first board 85. That is, the restricting portion 131 is a position restricting portion that restricts the arrangement position of the second board 91 with respect to the first board 85 while the second connector 90 is mounted on the first connector 80.

As described above, the gap between the side wall 133 and the side wall 134 in the widthwise direction is slightly larger than the width of the holding portion 99 of the second board 91. This makes it impossible for the operator to insert his/her finger into the space between the holding portion 99 of the second board 91 and the side wall 133 and the space between the holding portion 99 of the second board 91 and the side wall 134. Accordingly, the operator cannot detach the second board 91 from the first board 85 by inserting his/her finger into the gaps between the first side wall 133 of the restricting portion 131 and the holding portion 99 of the second board 91 and the gap between the side wall 134 of the restricting portion 131 and the holding portion 99 of the second board 91. Therefore, the operator can hold the holding portion 99 of the second board 91 only by inserting his/her finger from the proximal end side into the restricting portion 131.

When the operator tries to rotate the second board 91 in a horizontal rotating direction (the arrow R1 or R2 direction in FIG. 4) with respect to the first board 85 while holding the holding portion 99 of the second board 91, the finger holding the second board 91 comes into contact with the side walls 133 and 134 or the bottom portion 132. This restricts the movement of the second board 91 in a horizontal rotating direction with respect to the first board 85. This makes it impossible for the operator to detach the second board 91 from the first board 85 by rotating the second board 91 in a horizontal rotating direction with respect to the first board 85. That is, the restricting portion 131 restricts the movement of the second board 91 with respect to the first board 85 in directions (the arrow R1 and R2 directions in FIG. 4) other than the regulated detaching direction (the arrow T1 direction in FIG. 11). Preventing the second board 91 from being detached from the first board 85 in directions other than the regulated detaching direction will restrict the detaching direction of the second board 91 to only the regulated position. This makes it possible to safely release coupling between the first connector 80 and the second connector 90 and prevent unintentional loads from being applied to the connectors 80 and 90.

That is, when the second connector 90 is detached from the first connector 80, the restricting portion 131 restricts the moving direction (detaching direction) of the second board 91 with respect to the first board 85 to the regulated direction (the arrow T1 direction).

In this embodiment, the guiding portion 121 and the restricting portion 131 can be formed by bending the main body portion 101 of the shield case 77. This makes it possible to implement the board attaching structure 6 that allows easy attachment of the second board 91 and prevents the second board 91 from being detached along directions other than the regulated detaching direction without increasing the number of components. It is, therefore, possible to suppress an increase in cost and complexity of assembly work by increasing the number of components as compared with the case in which the shield case 77 is provided with another restricting member to prevent the second board 91 from being detached along directions other than the regulated detaching direction.

Note that the side walls 133 and 134 of the restricting portion 131 of the shield case 77 may not be perpendicular to the main body portion 101 and may be inclined with respect to the main body portion 101. In addition, the bottom portion 132 and the side walls 133 and 134 may be curved surfaces.

The restricting portion 131 may be formed by bending a portion extending from part of the left side edge portion 114 of the notched portion 111 to the right side. In this case as well, the restricting portion 131 is provided on the proximal end side of the guiding portion 121 along the longitudinal direction.

The restricting portion 131 may be constituted only by the first side wall 133 formed by bending an extended portion from the right side edge portion 113 of the notched portion 111 and the second side wall 134 formed by bending an extended portion from the left side edge portion 114 of the notched portion 111. In this case, the bottom portion 132 is not formed. In this case as well, providing the first side wall 133 and the second side wall 134 as a pair of wall surfaces can obtain the same effects as those in the above embodiment.

Note that the first connector 80 may be provided at a position closer (shifted) to one of the lower ends 127 and 128 of the inclined portions 125 and 126 than the middle portion between the lower ends 127 and 128. In this case as well, the first connector 80 is exposed outward through the guiding portion 121. In addition, in this case, the second connector 90 is preferably provided at a position shifted from the middle portion in the widthwise direction of the opposed surface 92. The second board 91 is preferably provided on the middle portion between the lower ends 127 and 128 of the inclined portions 125 and 126 while the first connector 80 is connected to the second connector 90.

The above board attaching structure 6 for the boards 85 and 91 can be applied other than the endoscope connector 5 of the endoscope 1. For example, this structure can be applied to a board coupling structure (not shown) provided in the control section 3 of the endoscope 1. In addition, the structure can be applied to a board coupling structure provided for other than the endoscope 1.

A board attaching structure (6) used in this embodiment includes a first board (85) formed in a plate shape, a first connector (80) provided on the surface (87) of the first board (85), a second board (91) formed in a plate shape, a second connector (90) provided on the second board (91) and connected to the first connector (80) to mount the second board (91) on the first board (85), a plate-like member (77) extending parallel to the first board (85) and covering at least part of the surface (87) of the first board (85), a posture restricting portion (121) formed by bending part of the plate-like member (77) toward the first board (85) and configured to restrict the posture of the second board (91) with respect to the first board (85) when the second connector (90) is mounted on the first connector (80), and a position restricting portion (131) formed by bending part of the plate-like member (77) and configured to restrict the position at which the second board (91) is arranged on the first board (85) while the second connector (90) is mounted on the first connector (80).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A board attaching structure comprising:
a first board formed in a plate shape;
a first connector provided on a surface of the first board;
a second board formed in a plate shape;
a second connector provided on the second board and connected to the first connector to mount the second board on the first board;
a plate-like member supported relative to the first board such that a first surface of the plate-like member extends above and parallel to the first board and covers at least part of the surface of the first board;
a posture restricting portion formed by bending part of the plate-like member toward the first board and configured to restrict a posture of the second board with respect to the first board when the second connector is mounted on the first connector; and
a position restricting portion formed by bending part of the plate-like member and configured to restrict a position at which the second board is arranged on the first board while the second connector is mounted on the first connector.

2. The board attaching structure according to claim 1, wherein the second board is a flat plate having an elongated shape, and
a surface area of a surface, of the second board, which faces the surface of the first board is smaller than a surface area of the surface of the first board.

3. The board attaching structure according to claim 1, wherein the posture restricting portion makes the first connector be exposed outside the plate-like member while the second connector is detached from the first connector, and restricts the position at which the second board is arranged on the first board when the second connector is mounted on the first connector.

4. The board attaching structure according to claim 1, wherein the posture restricting portion includes a pair of wall surfaces inclined toward the surface of the first board, and
each of the wall surfaces faces a side surface of the second board while the second connector is mounted on the first connector.

5. The board attaching structure according to claim 4, wherein the second board comprises a connector arrangement portion on which the second connector is arranged and a holding portion, and
the connector arrangement portion is exposed outside the plate-like member from between the wall surfaces while the second connector is mounted on the first connector.

6. The board attaching structure according to claim 1, wherein a surface of the second board which faces an opposite side to a surface facing the first board is closer to the first board than a second surface of the plate-like member which faces an opposite side to the first surface facing the first board while the second connector is mounted on the first connector.

7. The board attaching structure according to claim 1, wherein the position restricting portion restricts a moving direction of the second board with respect to the first board to a regulated direction when the second connector is detached from the first connector.

8. The board attaching structure according to claim 1, wherein the position restricting portion comprises a pair of wall surfaces inclined or orthogonal to the surface of the first board, and
each of the wall surfaces faces a side surface of the second board while the second connector is mounted on the first connector.

9. The board attaching structure according to claim 8, wherein the second board comprises a connector arrangement portion on which the second connector is arranged and a holding portion, and the holding portion is arranged between the wall surfaces while the second connector is mounted on the first connector.

10. The board attaching structure according to claim 1, wherein the first board comprises an electrical circuit electrically connected to the first connector.

11. The board attaching structure according to claim 1, wherein a signal cable is electrically connected to the second board.

12. The board attaching structure according to claim 1, wherein when the first connector is mounted on the second connector, the first board is electrically connected to the second board.

13. The board attaching structure according to claim 1, wherein the first surface is spaced from and faces the first connector.

14. The board attaching structure according to claim 1, wherein the plate-like member is supported by the first board.

15. The board attaching structure according to claim 14, wherein the plate-like member is directly or indirectly attached to the first board.

* * * * *